United States Patent [19]

Demus et al.

[11] Patent Number: 4,521,327
[45] Date of Patent: Jun. 4, 1985

[54] NEMATIC LIQUID CRYSTALS AND METHOD FOR PRODUCTION THEREOF

[75] Inventors: Dietrich Demus, Halle; Hans-Matthias Vorbrodt, Quedlinburg; Anton Hauser, Wettin; Jörg Vogel, Biesenthal; Horst Zaschke, Halle, all of German Democratic Rep.

[73] Assignee: VEB Werk für Fernsehelektronik im VEB Kombinat Mikroelektronik, Berlin, German Democratic Rep.

[21] Appl. No.: 463,377

[22] Filed: Feb. 3, 1983

[30] Foreign Application Priority Data

Feb. 17, 1982 [DD] German Democratic Rep. ... 237467
Feb. 17, 1982 [DD] German Democratic Rep. ... 237468

[51] Int. Cl.³ .................. C09K 3/34; C02F 1/13; C07D 319/06; C09K 11/06
[52] U.S. Cl. .................. 252/299.61; 252/299.5; 350/350 R; 350/350 S; 549/372; 549/376
[58] Field of Search ............ 549/369, 372, 376; 252/299.61, 299.5; 350/350 R, 350 S

[56] References Cited

U.S. PATENT DOCUMENTS

| | | | |
|---|---|---|---|
| 4,086,002 | 4/1978 | Arora | 252/299.67 |
| 4,200,580 | 4/1980 | Hsu | 252/299.61 |
| 4,298,528 | 11/1981 | Sethofer | 252/299.61 |
| 4,313,878 | 2/1982 | Hsu | 252/299.61 |
| 4,325,830 | 4/1982 | Sethofer et al. | 252/299.61 |
| 4,344,856 | 8/1982 | Demus et al. | 252/299.61 |
| 4,348,324 | 9/1982 | Demus et al. | 252/299.61 |
| 4,393,231 | 7/1983 | Misaki et al. | 252/299.5 |

FOREIGN PATENT DOCUMENTS

| | | | |
|---|---|---|---|
| 56501 | 7/1982 | European Pat. Off. | 252/299.61 |
| 3227916 | 3/1983 | Fed. Rep. of Germany | 252/299.61 |
| 2508032 | 12/1982 | France | 549/369 |
| 57-139074 | 8/1982 | Japan | 252/299.61 |
| 2067586 | 7/1981 | United Kingdom | 252/299.61 |
| 2092169 | 8/1982 | United Kingdom | 252/299.1 |

OTHER PUBLICATIONS

Banks, H. D., J. Org. Chem., vol. 46, No. 8, pp. 1743-1745 (1981).
Eliel, E. L. et al., JACS, vol. 94 (1), pp. 171-176 (1972).
Kaloustian, M. K. et al., JACS, vol. 98 (4), pp. 956-965 (1976).

*Primary Examiner*—Teddy S. Gron
*Attorney, Agent, or Firm*—Jordan & Hamburg

[57] ABSTRACT

The invention relates to nematic liquid crystals, especially for electro-optical components for the modulation of transmitted or reflected light, as well as for the display of numbers, symbols and images, exhibiting favorable physical characteristics, as well as to a method for the production of the new substances.

It has been found that new liquid crystal 2-substituted-1,3-dioxane-5-carboxylic acid esters of the general formula

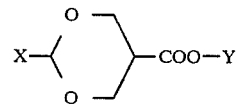

are suited for use in electro-optical components for the modulation of the light, as well as for the display of numbers, symbols and images, and can be used alone, in mixtures with each other and/or in mixtures with additional liquid crystal or non-liquid crystal substances.

In the method for the production of the new liquid crystal trans-2-substituted-1,3-dioxane-5-carboxylic acid esters, 2-substituted-1,3-dioxane carboxylic acids, with halogen donors such as thionyl chloride, sulfuryl chloride or phosphoric halides, preferably in the absence of organic bases, are converted into the corresponding acid chlorides, which are subsequently esterified in well-known fashion with alcohols or substituted phenols.

38 Claims, No Drawings

NEMATIC LIQUID CRYSTALS AND METHOD FOR PRODUCTION THEREOF

BACKGROUND OF THE INVENTION AND PRIOR ART STATEMENT

The invention relates to nematic liquid crystals in electro-optical components for the modulation of transmitted or reflected light, as well as for the display of figures, symbols and images, and to a method for the production of these new substances.

Liquid crystals, particularly the ones of the nematic type, are personified by anisotropy of optic, dimagnetic and electric characteristics. Because of these characteristics, nematic liquid crystals are successfully used in the manufacture of electro-optical components for the modulation of light, as well as for display of figures, symbols and images. Such components are extremely suitable as displays for electronic clocks, computers and other micro-electronical products.

New and increasingly higher demands are placed on the liquid crystal substances in displays to be used in modern devices, with the specific characteristics of these substances critically influencing the characteristics and application ranges of the displays. Since no pure compound exists which comes even close to meeting all the demands, mixtures of several compounds are almost always used. The characteristics of the mixtures are, to a large extent, determined and influenced by the individual mixed components. For the adjustment of the mixtures to all possible applications, many individual components of various categories of substances, with quite specific characteristics, may be needed. Besides substances with low melting temperatures and sufficiently high clear temperatures, substances with very low birefringence are needed, for example, in the case of new variations based on the Schadt-Helfrich-effect (twist cells). (G. Baur in: The Physics and Chemistry of Liquid Crystal Devices (1980), edited by G. J. Sprokel, Plenum Publ. Corp. New York 1980, p. 61).

The previously known dioxane derivatives have undesirably low clear points in part, or exhibit an undesirable tendency to forming smectic phases (e.g., the 5-n-alkyl-2-cyanophenyl-1,3-dioxane, WP 139852 and WP 139867; additionally, substituted cyclohexyl-dioxane, WP CO 9 K/232 636/0).

It is the object of the invention to provide new nematic liquid crystals with favorable physical characteristics, particularly regarding the melting- and clear temperatures, stability against thermal stress, light, and electrical fields, as well as low birefringence, as well as to provide a method for the production of these substances.

SUMMARY OF THE INVENTION

The invention has the object of developing new nematic liquid crystals on the basis of substituted 1,3-dioxanes with the required favorable characteristics, as well as developing a method for the production thereof.

It has been found that new liquid crystal 2-substituted-1,3-dioxane-5-carboxylic acid esters having the general formula

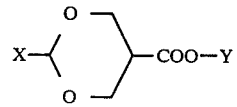

with

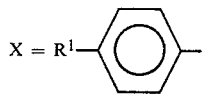 and $Y = R^2$ or $X = R^3$ and $Y = R^2$
or $X = R^3$ and $Y = R^4$ wherein
$R^1 = C_nH_{2n+1}$; $C_nH_{2n+1}O$; CN; $NO_2$; Halogen;

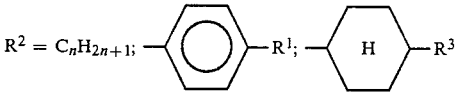

$R^3 = C_nH_{2n+1}$

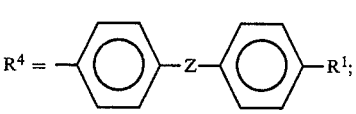

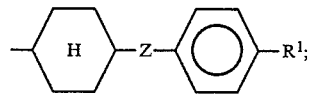

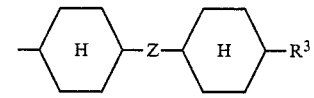

$Z = -COO-; -OOC-;$ and in which $n = 1$ to 10, are suitable for use in electro-optical components for the modulation of transmitted or reflected light as well as for the display of figures, symbols and images, either alone, in mixture with each other, and/or in mixture with other liquid crystal or non-liquid crystal substances.

DETAILED DESCRIPTION OF PREFERRED EMBODIMENTS

The following tables 1–4 contain examples of the substances according to the invention.

In these tables, the symbols used represent the following:

K = crystalline solid
S = smectic phase
N = nematic phase
is = isotropic liquid

TABLE 1
trans-2-subst.-1,3-dioxane-5-carboxylic acid-[4-cyanophenyl ester]
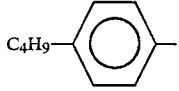
| Comp. | R | K | S | N | is |
|---|---|---|---|---|---|
| 1a | C₃H₇ | .88 | — | (.46) | . |
| 1b | C₄H₉ | .78 | — | (.27) | . |
| 1c | C₅H₁₁ | .81 | — | (.47) | . |
| 1d | C₆H₁₃ | .64 | — | (.47.5) | . |
| 1e | C₇H₁₅ | .68 | (.61) | — | . |
| 1f | C₈H₁₇ | .69.5 | .70 | — | . |
| 1g | C₉H₁₉ | .73 | .79 | — | . |
| Comp. | R | K | N | is |
|---|---|---|---|---|
| 1h | C₄H₉–⌬– | .109 | .181 | . |
| 1i | C₆H₁₃–⌬– | .131 | .167 | . |
| 1j | CH₃O–⌬– | .171 | .196 | . |
| 1k | C₂H₅O–⌬– | .126 | .212 | . |
| 1l | C₄H₉O–⌬– | .134 | .190 | . |
| 1m | C₅H₁₁O–⌬– | .135 | .188 | . |
| 1n | C₆H₁₃O–⌬– | .96 | .193 | . |
TABLE 2
trans-2-subst.-1,3-dioxane-5-carboxylic acid [4-subst.-phenyl ester]
| Comp. | R¹ | R² | K | S | N | is |
|---|---|---|---|---|---|---|
| 2a | C₉H₁₉ | –⌬–NO₂ | .70 | — | (.37) | . |
| 2b | C₆H₁₃ | –⌬–C₆H₁₃ | .39 | .74 | — | . |
| 2c | C₄H₉ | –⬡(H)–C₅H₁₁ | .<20 | .89 | — | . |
| 2d | C₆H₁₃ | –⬡(H)–C₅H₁₁ | .<20 | .97 | — | . |

TABLE 2-continued trans-2-subst.-1,3-dioxane-5-carboxylic acid [4-subst.-phenyl ester]

| Comp. | R¹ | R² | K | S | N | is |
|---|---|---|---|---|---|---|
| 2e | $C_6H_{13}$ | —⟨O⟩—$OC_6H_{13}$ | . 82 | . 93 | — | . |
| 2f | $C_6H_{13}$ | —⟨O⟩—$CH=C(CN)_2$ | . 90 | (.55) | — | . |
| 2g | $C_9H_{19}$ | —⟨O⟩—$CH=C(CN)_2$ | . 98 | (.94) | — | . |
| 2h | $C_6H_{13}$ | —⟨O⟩—$CH_2$—$CH_2$—CN | . 68 | — | — | . |
| 2i | $C_8H_{17}$ | —⟨O⟩—$CH_2$—$CH_2$—CN | . 77 | (.76) | — | . |
| 2j | $C_9H_{19}$ | —⟨O⟩—$CH_2$—$CH_2$—CN | . 80 | (.79.5) | — | . |

TABLE 3 trans-2-[4-subst.-phenyl]-1,3-dioxane-5-carboxylic acid or thiocarboxylic acid-[4-subst.-phenyl ester]

$R^1$—⟨O⟩—$\begin{matrix}O—\\O—\end{matrix}$〉—COX—⟨O⟩—$R^2$

| Comp. | R¹ | R² | X | K | S | N | is |
|---|---|---|---|---|---|---|---|
| 3a | $C_4H_9$ | $C_2H_5$ | O | . 99 | . 106 | . 128 | . |
| 3b | $C_4H_9$ | $NO_2$ | O | . 125 | — | . 132 | . |
| 3c | $C_2H_5O$ | $OC_7H_{15}$ | O | . 109 | . 159 | . 182 | . |
| 3d | $C_6H_{13}O$ | $NO_2$ | O | . 111 | — | . 168 | . |
| 3e | $C_6H_{13}O$ | $CH=CH(CN)_2$ | O | . 139 | — | . 169 | . |
| 3f | $C_4H_9$ | $NO_2$ | S | . 144 | — | . 174 | . |
| 3g | $C_4H_9$ | $C_2H_5$ | S | . 109 | (.106) | . 128 | . |
| 3h | $C_4H_9$ | $C_4H_5$ | S | . 92 | . 133 | | . |

TABLE 4

2-n-hexyl-1,3-dioxane-5-carboxylic acid-[4-subst.-phenoxy-carbonyl-phenyl ester]

$C_6H_{13}$—$\begin{matrix}O—\\O—\end{matrix}$〉—COO—⟨O⟩—COO—⟨O⟩—$R^1$
  with $R^2$ on middle ring

| Comp. | R¹ | R² | K | S | N | is |
|---|---|---|---|---|---|---|
| 4a | $CH_3$ | H | . 72 | . 200 | . 308 | . |
| 4b | $C_4H_9O$ | H | . 120 | . 199 | — | . |
| 4c | $C_7H_{15}O$ | $C_2H_5$ | . <20 | . 190 | — | . |

The substances according to the invention are characterized in part by low melting temperatures, especially when used in mixtures, in part by high clear temperatures, with all exhibiting high stability against chemical and thermal influences as well as against electric fields, and by having unusually small values regarding optical birefringence.

For the production of the new liquid crystal trans-2-substituted-1,3-dioxane-5-carboxylic acid esters, 2-substituted-1,3-dioxane carboxylic acids with halogen donors such as thionyl chloride, sulfuryl chloride or phosphoric halides, are transformed, preferably without organic bases, to the corresponding acid chlorides, which are subsequently esterified with alcohol or substituted phenols. This latter step is, in itself, already known.

Equation:

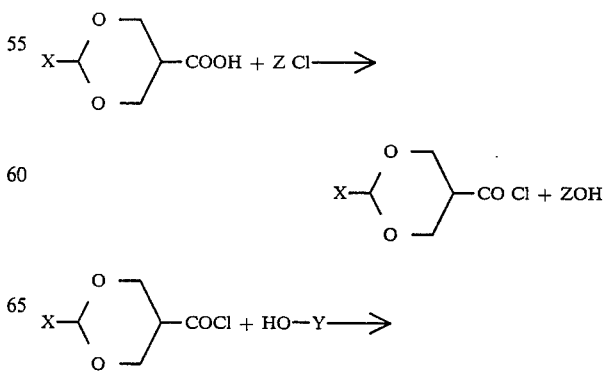

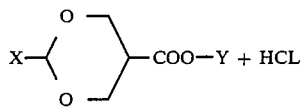

A surprising aspect of this conversion is that the substituted 1,3-dioxane-carboxylic acids are not hydrolyzed as cyclic acetates by the halogen donors, as is usually the case with 1,3-dioxanes.

The 2-substituted-1,3-dioxane-5-carboxylic acids are synthesizable, according to the synthesis listed in the literature for 2-isopropyl-1,3-dioxane-5-carboxylic acid, by reacting the corresponding aldehyde with bis-hydroxy-methylmalonic acid diethyl ester, with removal of water to form 2-isopropyl-1,3-dioxane-5,5-dicarboxylic acid diethyl ester, followed by hydrolysis and decarboxylizing (E. L. Eliel, H. D. Banke: J. Amer.Chem.Soc. 94, 171 (1972)). By modification of this rule, the production of 2-n-alkyl- and 2-(subst.aryl)-1,3-dioxane-5-carboxylic acids is made possible, which is not known from the literature. Esterification of the produced acid chlorides with alcohol or substituted phenols result in the previously unknown 2-substituted-1,3-dioxane-5-carboxylic acid esters. The isolated cis-trans-isomer mixture of the ester can be separated by fractional crystallization, since only the trans-isomers are capable of forming liquid crystal phases.

According to the method used in the invention, the basic and intermediate substances listed in Table 5 can be produced for the liquid crystal substances in the invention.

TABLE 5 trans-2-subst.-1,3-dioxane-5-carboxylic acids

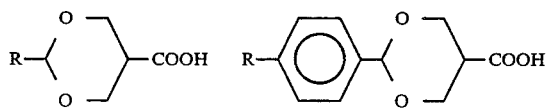

| Comp. | R | K | is | Comp. | R | K | is |
|---|---|---|---|---|---|---|---|
| 5a | C3H7 | . 114–115 | . | 5h | C4H9 | . 182–184 | . |
| 5b | C4H9 | . 115–117 | . | 5i | C6H13 | . 176–179 | . |
| 5c | C5H11 | . 120–121 | . | 5j | CH3O | . 181–182 | . |
| 5d | C6H13 | . 119–120 | . | 5k | C2H5O | . 179–182 | . |
| 5e | C7H15 | . 117–118 | . | 5l | C4H9O | . 181–184 | . |
| 5f | C8H17 | . 119–121 | . | 5m | C5H11O | . 181–183 | . |
| 5g | C9H19 | . 122–123 | . | 5n | C6H13O | . 176–178 | . |

The invention will be explained below by means of examples.

Examples 1 to 13 illustrate and analyze mixtures which contain the substances according to the invention.

The method of production according to the invention is established in examples 4 to 8.

EXAMPLE 1

In an electro-optical cell, on the basis of the Schadt-Helfrich effect, which is prepared according to conventional principle (Meier, G.; Sackmann, H.: Grabmaier, J. G.: Applications of Liquid Crystals, Berlin-Heidelberg-New York 1975), a mixture having the following composition was examined (composition in mol %)

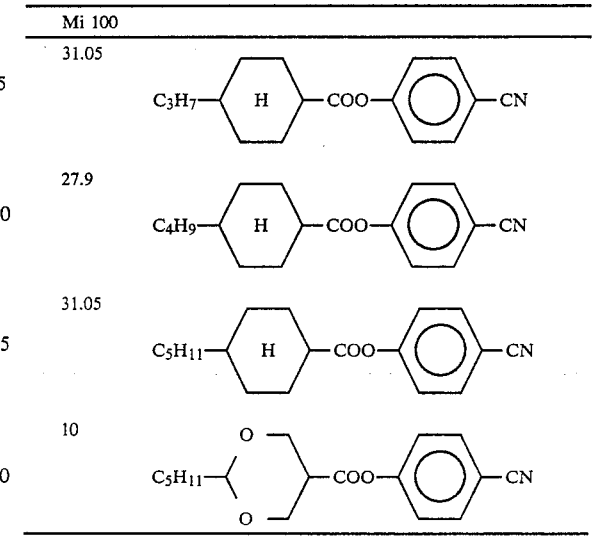

The mixture exhibited the following characteristics:

| K 1.5–6.5 | N 67.5 Is |
|---|---|
| Threshold voltage: | U - 1.4 V |
| Initiation time | $t_{E50\%}$ = 500 ms |
| Decay time | $t_{E50\%}$ = 180 ms |
| Layer thickness: | d = 12.1 /μm |
| Temperature: | t = 20° C. |

EXAMPLE 2

In a cell according to example 1, the following mixture was examined:

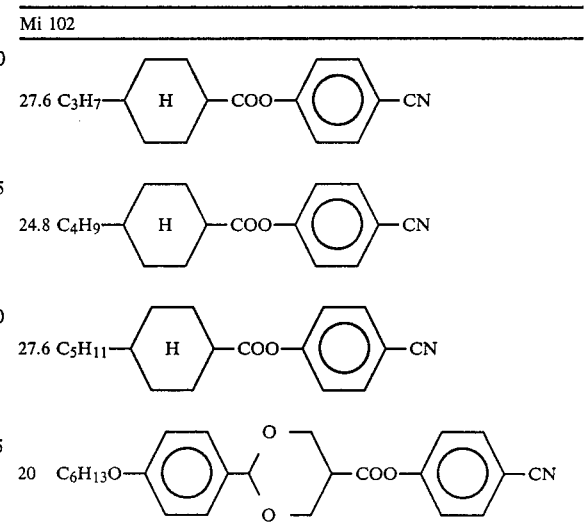

The mixture exhibited the following characteristics:

| K 3–9 | N 101–105 Is |
|---|---|
| Threshold voltage: | U = 1.4 V |
| Initiation time: | $t_{E50\%}$ = 620 ms |
| Decay time: | $t_{A50\%}$ = 170 ms |
| Layer thickness: | d = 12.0 /μm |
| Temperature: | T = 20° C. |

EXAMPLE 3

The following mixture was examined in a cell according to example 1:

| Mi 103 | |
|---|---|
| 27.6 | 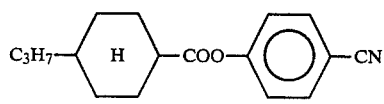 |
| 24.8 | 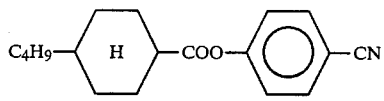 |
| 27.6 | 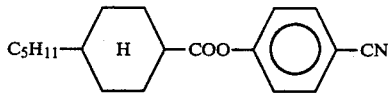 |
| 20 | 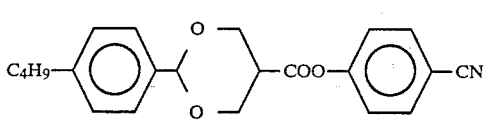 |

The mixture exhibited the following characteristics:

| | |
|---|---|
| K 9-11 | N 95-98 Is |
| Threshold voltage: | U = 1.5 V |
| Initiation time: | $t_{E50\%}$ = 1010 ms |
| Decay time: | $t_{A50\%}$ = 230 ms |
| Layer thickness: | d = 13.5 /µm |
| Temperature: | T = 20° C. |

EXAMPLE 4

Production of 2-(4-n-hexoxyphenyl)-1,3-dioxane-5-carboxylic acid (5n)

20.6 g (0.1 mol) 4-n-hexoxybenzaldehyde and 24.2 g (0.11 mol) bis-hydroxymethyl-malonic acid-diethyl ester are heated in 150 ml benzene in a corresponding amount of 0.2 g p-toluenesulfonic acid, while stirring for 8 hours. After cooling, the benzene is carefully washed with 2% NaHCO₃ solution, then with water, and then distilled under vacuum (rotating evaporator), with the residue being recrystallized from alcohol (2-(4-n-hexoxyphenyl)-1,3-dioxane-5,5-dicarboxylic acid-diethyl ester I). The yield at I is 31 g (76% of theoretical). I melts at 30° C. (from n-hexane). 31 g (0.074 mol) I and 18 g (0.32 mol) KOH in 150 ml 95% ethanol is heated for one hour at reflux in the continued preparation. Ethanol is then distilled from the reaction residue, water added to the residue, and the aqueous phase concentrated to 30-50 ml. After addition of 100 ml ether, it is cooled to 0° C. and concentrated HCl is added while stirring (up to pH 1). Subsequently, the ether fraction is immediately separated, washed with water, dried with Na₂SO₄, and the solvent removed in the rotating evaporator. The residue (16.5 g, 62% of theoretical) of 2(4-n-hexoxyphenyl)-1,3-dioxane-5,5-dicarboxylic acid (decomposition above 135° C.) is decarboxylized with a water jet vacuum pump at 120° to 170° C. Having completed the brisk CO₂ development, the residue of benzene or cyclohexane is recrystallized. The yield of 5 n is 63% of theoretical. The melting point of 5 n is 176° to 178° C. Additional examples are listed in Table 5.

EXAMPLE 5

Production of 2-n-hexyl-1,3-dioxane-5-carboxylic acid (5d)

2-n-hexyl-1,3-dioxane-5,5-dicarboxylic acid II is produced analogous to Example 4 from 114 g (1 mol) heptanol and 242 g (1.1 mol) bis-hydroxymethyl-malonic acid-diethyl ester. 26 g (0.01 mol) II are decarboxylized in the presence of 15 mol abs. pyridine or quinolin while stirring and with moisture excluded from the reflux (2 hours). After cooling, it is acidified (dropwise) with 20% HCl and the solution extracted with ether several times. The combined ether extracts are each washed once with 50 ml 10% HCl and saturated NaCl solution, dried with Na₂SO₄, and the residue recrystallized from cyclohexane following removal of the solvents in the rotating evaporator.

Yields of 5d: 18 g (85% of theoretical), Fp: 119°-120° C.

EXAMPLE 6

Production of 2-n-hexyl-1,3-dioxane-5-carboxylic acid-(4-cyclophenyl ester) (1d)

1.08 g (0.01 mol) 5d is dissolved in 10 ml abs. ether, with 0.4 ml abs. pyridine then being added, and followed by cooling with an ice-salt mixture to 0° to 10° C. Subsequently, 0.6 g thionyl chloride is added dropwise and suctioned off from separated residue (pyridine hydrochloride) after an hour. The produced acid chloride (mother lye) is stirred for approximately 2-3 hours at room temperature after adding 5 ml abs. pyridine and 1.3 g (0.01 mol) 4-hydroxybenzonitrile. Thereafter, the reaction residue is treated with 50 ml of ether, washed with water and NaHCO₃ solution, dried with Na₂SO₄, and the solvent distilled off in the rotating evaporator. The residue is recrystallized from methanol.

Yields of 1d: 0.5 g (37% of theoretical); K64 (N47.5) is

EXAMPLE 7

Production of 2-n-octyl-1,3-dioxane-5-carboxylic acid-(4-cyanophenyl ester) (1f)

2.44 g (0.01 mol) 2-n-octyl-1,3-dioxane-5-carboxylic acid 5f was heated with 2 ml thionyl chloride excluding moisture until gas development during reflux is completed (approximately 20 minutes). Thereafter, the extraneous thionyl chloride is distilled off in the water jet pump vacuum, the residue added to abs. pyridine (5 ml), and stirred with 1.3 g (0.01 mol) 4-hydroxybenzonitrile for 2-3 hours at room temperature. The residue is poured over ice, the separated residue recrystallized several times from methanol or absorbed in ether, washed with 1n-KOH-solution, 10% HCl and H₂O, dried with Na₂SO₄, the solvent distilled off and the residue recrystallized from methanol.

Yields of 1f: 45% of theoretical: K 69.5 S 70.5 is

EXAMPLE 8

Production of 2-4-n-hexylphenyl-1,3-dioxane-5-carboxylic acid-(4-cyanophenyl ester) (1i)

2.16 g (0.007 mol) 5i, 0.8 g (0.007 mol) 4-hydroxybenzonitrile, 1.45 g (0.007 mol) dicyclohexylcarbodiimide, 0.55 (0.007 mol) pyridine are stirred in 50 ml abs. ether for 3 hours at room temperature. Subsequently, the resultant residue is filtered off, and the filtrate washed with water, 2% NaHCO₃ solution and water. The ether extract is dried with Na₂SO₄, the solvent distilled off in the rotating evaporator and the residue recrystallized several times from methanol.

Yields of 1i: 1.7 g (60% of theoretical); K 131 N 167 is

We claim:

1. A 2-substituted-1,3-dioxane-5-carboxylic acid ester having the general formula

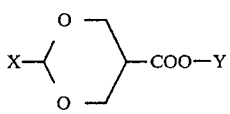

in which X = R¹—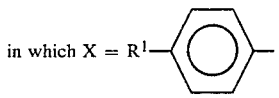 and Y = R² or R⁵ or X = R³ and Y = R⁵
or X = R³ and Y = R⁴
wherein R¹ = $C_nH_{2n+1}$; $C_nH_{2n+1}O$; CN; NO₂;
R² = $C_nH_{2n+1}$;
R³ = $C_nH_{2n+1}$ R⁴ = 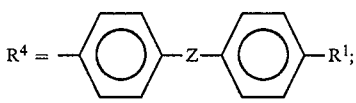

R⁵ = 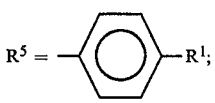

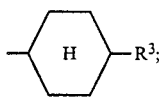

Z = —COO—;

with n=1 to 10.

2. Trans-2-n-propyl-1,3-dioxane-5-carboxylic acid-(4-cyanophenyl ester) according to claim 1.
3. Trans-2-n-butyl-1,3-dioxane-5-carboxylic acid-(4-cyanophenyl ester) according to claim 1.
4. Trans-2-n-pentyl-1,3-dioxane-5-carboxylic acid-(4-cyanophenyl ester) according to claim 1.
5. Trans-2-n-hexyl-1,3-dioxane-5-carboxylic acid-(4-cyanophenyl ester) according to claim 1.
6. Trans-2-n-heptyl-1,3-dioxane-5-carboxylic acid-(4-cyanophenyl ester) according to claim 1.
7. Trans-2-n-octyl-1,3-dioxane-5-carboxylic acid-(4-cyanophenyl ester) according to claim 1.
8. Trans-2-n-nonyl-1,3-dioxane-5-carboxylic acid-(4-cyanophenyl ester) according to claim 1.
9. Trans-2-n-nonyl-1,3-dioxane-5-carboxylic acid-(4-nitrophenyl ester) according to claim 1.
10. Trans-2-n-hexyl-1,3-dioxane-5-carboxylic acid-(4-n-hexylphenyl ester) according to claim 1.
11. Trans-2-n-butyl-1,3-dioxane-5-carboxylic acid-(4-n-pentyl cyclohexyl ester) according to claim 1.
12. Trans-2-n-hexyl-1,3-dioxane-5-carboxylic acid (4-n-pentyl cyclohexyl ester) according to claim 1.
13. Trans-2-n-hexyl-1,3-dioxane-5-carboxylic acid-(4-n-hexoxy phenyl ester) according to claim 1.
14. Trans-2-n-hexyl-1,3-dioxane-5-carboxylic acid-(4-(2,2'-dicyanoethenyl)-phenyl ester).
15. Trans-4-n-nonyl-1,3-dioxane-5-carboxylic acid-(4-(2,2'-dicyanoethenyl)-phenyl ester).
16. Trans-4-n-hexyl-1,3-dioxane-5-carboxylic acid-(4-cyanoethylphenyl ester).
17. Trans-4-n-octyl-1,3-dioxane-5-carboxylic acid-(4-cyanoethylphenyl ester).
18. Trans-4-n-nonyl-1,3-dioxane-5-carboxylic acid-(4-cyanoethylphenyl ester).
19. Trans-2-(4-n-butylphenyl)-1,3-dioxane-5-carboxylic acid-(4-ethylphenyl ester).
20. Trans-2-(4-n-hexoxyphenyl)-1,3-dioxane-5-carboxylic acid-(4-(2,2'-dicyanoethenyl)-phenyl ester).
21. 2-n-hexyl-1,3-dioxane-5-carboxylic acid-(4-(4-methylphenoxycarbonyl)-phenylester) according to claim 1.
22. 2-n-hexyl-1,3-dioxane-5-carboxylic acid-(4-(4-n-butoxyphen oxycarbonyl)-phenyl ester) according to claim 1.
23. 2-n-hexyl-1,3-dioxane-5-carboxylic acid-(4-(4-n-heptoxy-phenoxycarbonyl)-2-ethylphenyl ester).
24. Trans-2-(4n-butylphenyl)-1,3-dioxane-5-carboxylic acid-(4-cyanophenylester) according to claim 1.
25. Trans-2-(4-n-hexylphenyl)-1,3-dioxane-5-carboxylic acid-(4-cyanophenylester).
26. Trans-2-(4-methoxyphenyl)-1,3-dioxane-5-carboxylic acid-(4-cyanophenylester).
27. Trans-2-(4-ethoxyphenyl)-1,3-dioxane-5-carboxylic acid-(4-cyanophenylester).
28. Trans-2-(4-n-butoxyphenyl)-1,3-dioxane-5-carboxylic acid-(4-cyanophenylester).
29. Trans-2-(4-n-pentoxyphenyl)-1,3-dioxane-5-carboxylic acid-(4-cyanophenylester).
30. Trans-2-(4-n-hexoxyphenyl)-1,3-dioxane-5-carboxylic acid-4-cyanophenylester).
31. Trans-2-(4-n-butylphenyl)-1,3-dioxane-5-carboxylic acid-(4-nitrophenyl ester) according to claim 1.
32. Trans-2-(4-n-ethoxyphenyl)-1,3-dioxane-5-carboxylic acid-(4-n-heptoxyphenylester) according to claim 1.
33. Trans-2-(4-n-hexoxyphenyl)-1,3-dioxane-5-carboxylic acid-(4-nitrophenylester) according to claim 1.
34. Trans-2-(4-n-butylphenyl)-1,3-dioxane-5-thiocarboxylic acid-(4-ethyl phenyl ester).
35. Trans-2-(4-n-butylphenyl)-1,3-dioxane-5-thiocarboxylic acid-(4-n-butylphenyl ester).
36. An electro-optical device for modulation of transmitted or reflected light, or for display of numbers, symbols and images, containing a nematic, liquid crystal compound of claim 1.
37. Trans-2-(4-n-butyl-phenyl)-1,3-dioxane-5-thiocarboxylic acid-(4-nitrophenyl ester).
38. A 2-substituted-1,3-dioxane-5-carboxylic acid ester having the general formula

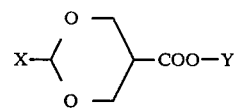

in which

X = R¹—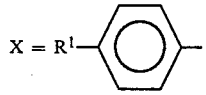 and Y = R²

-continued
or $X = R^3$ and $Y = R^4$
wherein
$R^1 = C_nH_{2n+1}$; $C_nH_{2n+1}O$; CN; NO$_2$;
$R^2 = C_nH_{2n+1}$; 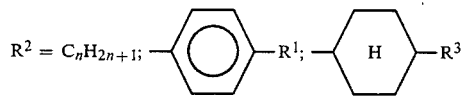
-continued
$R^3 = C_nH_{2n+1}$
$R^4 = $ 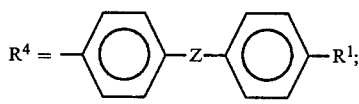
$Z = -COO-$;
with $n = 1$ to 10.
* * * * *